United States Patent [19]

Talbert

[11] 4,138,883
[45] Feb. 13, 1979

[54] PORTABLE DEVICE FOR MEASURING 25 PERCENT R.M.A. COMPRESSION VALUES

[76] Inventor: Miles E. Talbert, P.O. Box 1901, High Point, N.C. 27260

[21] Appl. No.: 824,358

[22] Filed: Aug. 15, 1977

[51] Int. Cl.² ............................................. G01N 3/14
[52] U.S. Cl. .................................................. 73/818
[58] Field of Search ..................................... 73/94, 81

[56] References Cited

U.S. PATENT DOCUMENTS

| | | | |
|---|---|---|---|
| 1,483,565 | 2/1924 | Adams | 73/81 |
| 1,894,490 | 1/1933 | Hobson | 73/81 |
| 2,913,899 | 11/1959 | Wohler | 73/94 |
| 3,786,676 | 1/1974 | Korolyshun et al. | 73/94 |
| 4,004,457 | 1/1977 | Eide et al. | 73/94 |

Primary Examiner—Anthony V. Ciarlante

[57] ABSTRACT

A conventional strain gage mechanism is mounted within a support bracket having at least an end wall or plate through which the plunger of the strain gage extends. The dial of the strain gage is so arranged and calibrated as to be representative of 25% R.M.A. compression values responsive to a force applied against the free end of the plunger. The end plate insures that the device is applied consistently against different pieces of compressible material.

3 Claims, 3 Drawing Figures

PORTABLE DEVICE FOR MEASURING 25 PERCENT R.M.A. COMPRESSION VALUES

BACKGROUND OF THE INVENTION

In the foam industry, which includes the foaming of polymeric composition and fabrication of the resulting foam material into mattresses, seat cushions, and the like, a standard indication of firmness of such materials is known as the R.M.A. compression value. By way of information, R.M.A. is the abbreviation for Rubber Manufacturers Association, and the foam industry generally conforms to this association's specifications for the compression test to be used in measuring foam material for compression modulus.

Such test involves measuring the weight necessary to produce a 25% indentation in a sample of foam by bringing a flat circular plate having an area of fifty square inches and a preload of one pound in contact with the surface of the foam piece to determine the initial thickness thereof. The material is then compressed 25% of the original height by increasing the load on the plate. The final total load is recorded as the R.M.A. compression value.

It has become conventional in the foam industry to continuously extrude foam in large buns, from which mattresses and cushions are later cut. It is very advantageous to be able to determine the compression value of a bun while it is being run or at sometime before it is cut, rather than after the bun has been sawed and cut into smaller pieces, or to easily measure and test a sample while it is being stored. Heretofore, such measurements have not been possible, because the measuring devices have required removal of a sample or slab of foam to a testing site, where the foam is laid on a flat plate, then the afore-described procedure for the R.M.A. compression value test is carried out. It is easily seen that this requires considerable interruptions in the normal flow of material and continuous testing or spot-checking at any time and at any place is not possible.

One example of an attempt to provide a more economical compression testing apparatus is illustrated and described in the U.S. Pat. No. 2,913,899 to Wohler, which does provide a portable device from the standpoint that the device may be moved around. However, it is still necessary to remove the foam slab, after cutting, from its assembly line or storage place and place it on a flat plate at which time the Wohler device may be utilized to effect the R.M.A. compression test. Additionally, test apparatus must be applied from the top and the process is relatively slow in that weights must be added at increments until the scale indicated ¾ of the thickness is reached.

SUMMARY OF THE PRESENT INVENTION

The present invention, on the other hand, is directed to a portable, hand-held device that may be carried by an operator or inspector and placed into position against the surface of any compressible foam materials, large or small. The device may be held at any orientation to obtain a reasonably accurate indication of the 25% R.M.A. compression value. It differs from prior devices in that it may be used at anyplace, no samples have to be cut, no pieces have to be removed and taken to a testing site, in fact no movement or disturbance of the ordinary processing of the foam occurs at all. Further, the device is relatively inexpensive to manufacture and easy to use. Variance of results from use of this device can be easily maintained within a 5% tolerance range.

Structure-wise, the present invention includes an ordinary strain gage, which is a spring-operated device having a plunger extending outwardly therefrom and a disc or button on the free end of the plunger representative of a reference point. The reference point is initially placed against the surface of the foam material being tested. As the device is then moved a prescribed distance, the firmness of the foam material against the button causes the plunger to move against the spring tension within. The dial includes a needle which moves indicative of the distance moved by the plunger during movement of the entire device. In the present invention, the only modification to the conventional strain gage is that the dial face is modified so that the readings thereon are representative of a range of 25% R.M.A. compression values. The strain gage is placed within a bracket having an end plate or wall with an opening therein through which the plunger extends. The end plate insures that the entire device is moved the prescribed distance after the button is placed against the surface of the foam.

In use, the operator carries the device in his hand and makes periodic samples by merely placing the device into contact with a surface of a piece of foam to be measured. He pushes the device up against the foam until the end plate lies flat against the surface with no apparent visual indentation thereof. During manufacture, the dial is zeroed and so calibrated with respect to a standard piece of foam, that in use the reading on the dial is a reasonably accurate indication of the 25% R.M.A. compression value.

It is therefore an object of the present invention to provide a portable compression testing device which facilitates the making of periodic, on-location tests of the 25% R.M.A. compression value of selected compressible materials.

It is another object of the present invention to provide a testing device of the type described which may be used merely by pushing the device against a compressible foam surface in any existing location and in any direction.

Other objects and a fuller understanding of the present invention will be apparent from reading the following detailed description of a preferred embodiment along with the accompanying drawings in which.

DETAILED DESCRIPTION OF A PREFERRED EMBODIMENT

Figure 1:
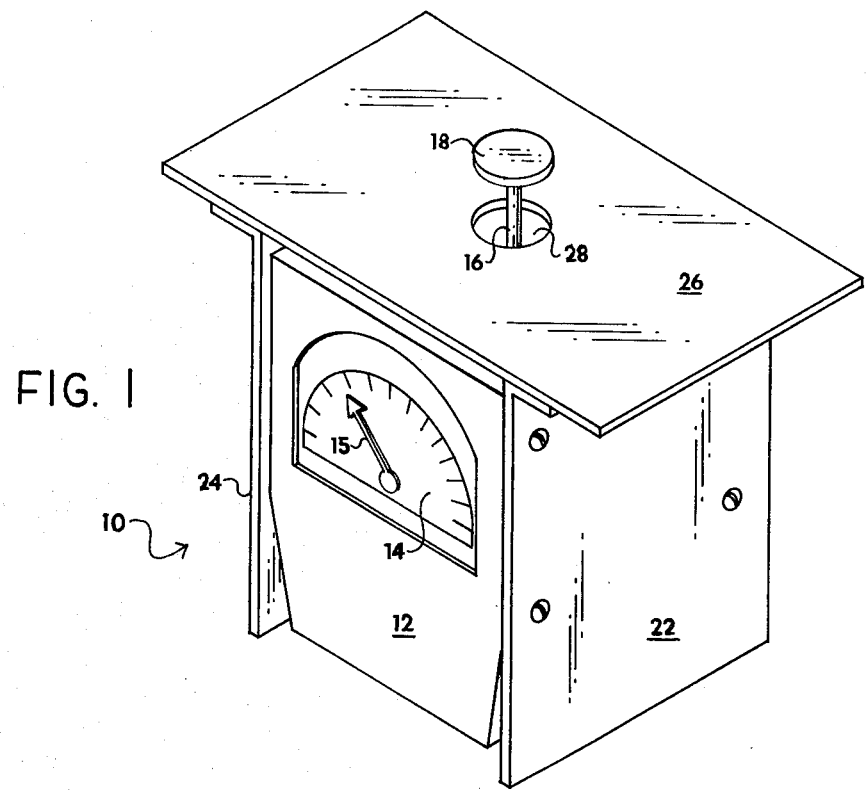
FIG. 1 is a perspective view of the device according to the present invention.

Turning now to the drawings, and particularly to FIG. 1, there is illustrated the testing device 10 according to the present invention which includes in general a strain gage 12 mounted within a frame or bracket having an end plate 26 through which the plunger 16 of the strain gage means 12 extends.

The strain gage means 12 includes a dial 14 and plunger 16 which terminates in a disc or button 18 lying in a plane transverse to the axis of the plunger 16. The inner mechanism of the gage is conventional in having a spring element 17 connecting plunger 16 with a rotating shaft onto which needle 15 is attached. Pressure against the plunger causes a resulting deflection in the needle which is an indication of the force applied. The dial 14 is so arranged and calibrated that rather than reading pounds of force exerted on the plunger, the dial 14 indicates 25% R.M.A. compression values, which are directly proportional to the resultant force exerted against button 18 by a piece of foam when the device is moved a prescribed distance toward the foam from a reference point. A zero adjustment knob 20 is so connected to the instrumentation within that the dial 14 may be set at zero value and thus continually adjusted.

While many types of strain gages would be applicable to the present invention, applicant has found that the Ametek Strain gage, Model 2TP, manufactured by Hunter Spring Division of Ametek Corp., Hatfield, Pennsylvania, is particularly suited to the present invention.

Figure 2:
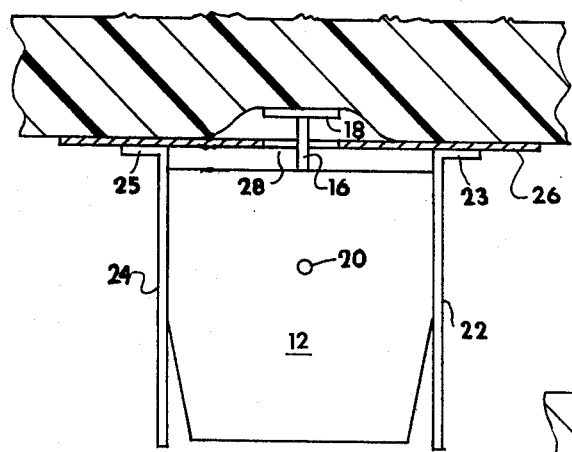
FIG. 2 is a partial cross-sectional view of the device according to the present invention in use against one surface of a piece of compressible foam material.

The bracket means into which the gage is mounted includes a pair of side walls 22, 24 having any suitable retaining means therein for receiving and holding the gage 12. Such retaining means, while not shown, might includes screw fasteners, spring arms, clips, and the like. Side walls 22, 24 extend parallel to each other in spaced relation along opposite sides of the gage 12. A pair of end flanges 23, 25 are bent outwardly from one end of side walls 22, 24 to provide flat areas against which end plate 26 may be positioned and spotwelded thereto. End plate 26 includes a generally central opening 28 therein through which the plunger 16 extends, as is better illustrated in FIG. 2. Initially the button 18 is extended beyond end wall 26 a prescribed distance a to locate a reference or zero point at which no force is exerted against button 18, but beyond which button 18 and thus plunger 16 meets resistance. When the device is moved toward the foam until end wall 26 engages the surface, plunger 16 will move a lesser distance b toward the wall 26 due to the pressure from the foam.

Figure 3:
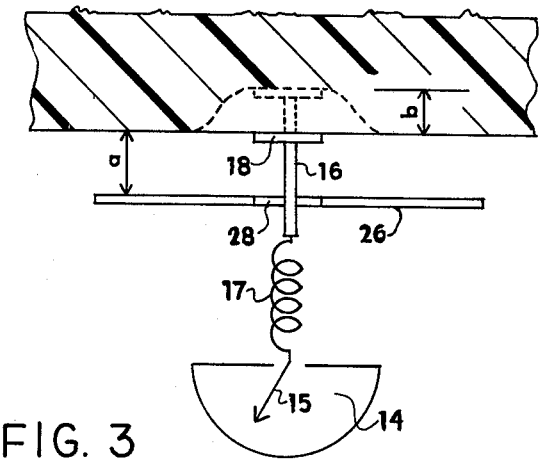
FIG. 3 is a schematic representation of the device of the present invention and its principle of operation.

In use, as illustrated in FIG. 3, the device is zeroed, then placed against any flat surface of foam, whether it be a side surface, bottom surface, top surface, or the like. The device is pushed against the side surface of the foam F (dotted lines in FIG. 3) until the end plate 26 is flat against the side surface, but does not significantly compress the foam. The reading on the scale 14 indicates the R.M.A. compression value of that particular piece of foam F. The plate 26 provides a visual means for insuring that the plate is moved the same distance each time a measurement is made from a reference point (the end of the button 18 in its normally extended position). This gives a very workable, reliable reading, which has been found to be accurate to within ±5%, which is an extremely workable tolerance. The reason this tolerance is so acceptable is that this device is designed for use throughout the foam forming operation, wherein often it is desired to know whether a piece of foam exhibits a 25% R.M.A. value of 20 or 35, and not whether it exhibits a 25% R.M.A. value of 22.4 and 22.5.

There is thus provided a portable, hand-held device for measuring 25% R.M.A. compression values of a compressible material without requiring movement of the test piece or separation therefrom the remainder of the material. This device is very accurate for the intended use, and may be used anywhere in a manufacturing plant on any piece at any orientation. The device is inexpensive, as well as being susceptible of quick use, and results in substantially better quality control within the manufacturing plant.

It is obvious that while a preferred embodiment of the present invention has been illustrated and described in detail above, various changes and modifications might be made without departing from the scope of the invention. For example, almost any type of bracket which includes an end wall through which the plunger of the strain gage may be extended, could be utilized as described hereinabove.

What is claimed is:

1. A portable device for determining approximate 25% R.M.A. compression values of a compressible material without requiring movement of the test piece or separation of any portion of the material from the remainder, said device comprising:
   (a) a strain gage means having a dial and a plunger extending outwardly therefrom and movable along the longitudinal axis of the plunger between a normal extended position and a second retracted position, said plunger terminating in a flat disc lying in a plane transverse to the axis of said plunger, said plunger and dial being so connected that readings on said dial change responsive to the force exerted against the end of the plunger, indicia on said dial calibrated with respect to movement of said plunger to represent approximate 25% R.M.A. values;
   (b) a bracket means for mounting said gage and including a flat end plate having an opening therein through which said plunger extends a normal prescribed distance, the plane of said disc being parallel to the plane of said end plate; and
   (c) said bracket means with said gage therein being of such size as to be easily carried in a workman's hand, whereby when said gage is urged against a compressible material in any direction, readings representative of 25% R.M.A. compression values accurate to within ±5% are visible on said dial.

2. The device according to claim 1, wherein the distance between the end plate and disc in the normal position exceeds the distance the plunger is moved between said normal and said second position.

3. A portable, hand-held device for determining approximate 25% R.M.A. compression values on a compressible material during and without interrupting the normal production and handling procedures, said device comrpising:
   (a) strain gage means including a movable plunger, an indicator means, and a spring means connecting said plunger and indicator means, whereby movement of said plunger causes a resulting deflection of said indicator means, the free end of said plunger including a flat disc secured thereto, the plane defined by said disc being transverse to the longitudinal axis of said plunger;
   (b) a base plate stationarily attached to said gage, whereby said plunger is movable relative to said plate, said base plate being normally fixed at a point spaced a first distance from the free end of said plunger;
   (c) said indicator means provided with a scale having indicia representative of various 25% R.M.A. compression values;
   (d) whereby when said plunger is placed against a test piece and said base plate is moved through said first distance, said plunger is caused to move inwardly toward said base plate resulting in a deflection of said indicator means readable on said scale as a 25% R.M.A. compression value within a 5% tolerance range.

* * * * *